United States Patent [19]

Walasek et al.

[11] Patent Number: 5,050,596
[45] Date of Patent: Sep. 24, 1991

[54] REUSABLE AND MICROWAVABLE HOT OR COLD THERAPY MITT AND METHOD OF MANUFACTURE

[75] Inventors: Steven P. Walasek; Stuart J. Walasek, both of Shavertown, Pa.

[73] Assignee: Packaging Electronics & Devices Corp., Nanticoke, Pa.

[21] Appl. No.: 605,460

[22] Filed: Oct. 30, 1990

Related U.S. Application Data

[63] Continuation-in-part of Ser. No. 448,864, Dec. 12, 1989.

[51] Int. Cl.$^5$ .............................................. A61F 7/00
[52] U.S. Cl. ...................................... 128/381; 128/382; 2/158
[58] Field of Search ............... 128/402, 379, 403, 399, 128/381, 382, 156; 62/259.3, 530; 383/901; 165/46; 2/18, 158, 159; 126/263

[56] References Cited

U.S. PATENT DOCUMENTS

| 558,604 | 4/1896 | Engel | 2/164 |
|---|---|---|---|
| 1,970,081 | 8/1934 | Ellondrath | 128/402 |
| 2,275,206 | 3/1942 | Sutherland | 2/18 |
| 2,515,298 | 7/1950 | Feldman | 128/381 |
| 2,842,771 | 7/1958 | Foti | 2/164 |
| 3,114,915 | 12/1963 | Gross | 2/164 |
| 3,506,013 | 4/1970 | Zdenek | 128/402 |
| 3,596,666 | 3/1971 | Murphy | 128/402 |
| 3,632,966 | 1/1972 | Aron | 128/402 |
| 3,763,622 | 10/1973 | Stanley, Jr. | 128/403 |
| 3,780,537 | 12/1973 | Spencer | 62/530 |
| 3,804,077 | 4/1974 | Williams | 126/263 |
| 3,874,000 | 4/1975 | Altman | 128/381 |
| 3,874,504 | 4/1975 | Verakas | 206/219 |
| 3,885,403 | 5/1975 | Spencer | 62/530 |
| 3,893,834 | 7/1975 | Armstrong | 62/4 |
| 4,021,640 | 5/1977 | Gross et al. | 128/381 |
| 4,055,188 | 10/1977 | Pelton | 128/402 |
| 4,092,982 | 6/1978 | Salem | 128/82.1 |
| 4,114,620 | 9/1978 | Moore et al. | 128/254 |
| 4,243,041 | 1/1981 | Paul | 128/402 |
| 4,381,025 | 4/1983 | Schooley | 128/402 |
| 4,462,224 | 7/1984 | Dunshee et al. | 62/530 |
| 4,488,552 | 12/1984 | McCann et al. | 128/402 |
| 4,596,250 | 6/1986 | Beisang, III et al. | 128/402 |
| 4,671,267 | 6/1987 | Stout | 128/156 |
| 4,756,311 | 7/1988 | Francis, Jr. | 128/403 |

FOREIGN PATENT DOCUMENTS

| 2457193 | 6/1976 | Fed. Rep. of Germany | 128/403 |
|---|---|---|---|
| 1383586 | 2/1975 | United Kingdom . | |

*Primary Examiner*—Edward M. Coven
*Assistant Examiner*—Mark S. Graham
*Attorney, Agent, or Firm*—Joseph Scafetta, Jr.

[57] ABSTRACT

A reusable and microwavable hot or cold therapy mitt for a user's hand has a bottom laminate, a first pocket containing a gel, a middle laminate being positioned above the first pocket, a second pocket being provided with an open air space for receiving the user's hand above the middle laminate, a layer of open-celled material being positioned above the second pocket, a layer of insulative wadding being placed above the layer of open-celled material, a third pocket being provided with dead air space for additional insulating above the layer of insulative wadding, and a top laminate being positioned above the third pocket. A strap fastens the therapy mitt securely on the user's hand. A method is also disclosed for manufacturing the therapy mitt. The bottom, middle and top laminates each have outer peripheral edges that are bonded together by a radio frequency (RF) heat-sealing step with outer peripheral edges of the layer of open-celled material and of the layer of insulative wadding.

16 Claims, 2 Drawing Sheets

REUSABLE AND MICROWAVABLE HOT OR COLD THERAPY MITT AND METHOD OF MANUFACTURE

CROSS-REFERENCE TO RELATED APPLICATION

This application is a continuation-in-part (CIP) application of U.S. patent application Ser. No. 07/448,864 filed on Dec. 12, 1989, pending and commonly assigned by the same two inventors to the same assignee.

BACKGROUND OF THE INVENTION

1. Field of the Invention

The present invention relates to a therapeutic compress and, in particular, to a reusable and microwavable hot or cold therapy mitt. The invention also relates to a method for manufacturing such a therapy mitt.

2. Description of the Related Art

Heat therapy is a recommended treatment for relieving minor pain caused by muscle aches, soreness, stiffness, cramps, and arthritis. The therapy works by providing heat through the skin to the affected muscles to dilate the blood vessels therein and, thus, to increase the circulation of the blood therethrough. For many years, this heat therapy has been provided via a hot compress which was held against the affected portion of the body.

Cold therapy is a recommended treatment for relieving minor pain caused by injuries to muscles which swell in response to such injuries. This cold therapy works by withdrawing heat through the skin from the injured muscles to constrict the blood vessels therein and, thus, to reduce swelling by decreasing the circulation of the blood through such injured muscles. Such a cold therapy pack is shown in U.S. Pat. No. 4,243,041 which issued to Malcolm D. Paul on Jan. 6, 1981.

Also, manufacturers have developed compresses that can serve to provide either hot or cold therapy. Examples of compresses that serve to provide either hot or cold therapy are the prior art packs shown in the following references:

| Country | Patent No. | Inventor(s) | Issue Date |
| --- | --- | --- | --- |
| U.S. | 3,763,622 | Stanley, Jr. | Oct. 09, 1973 |
| U.S. | 3,780,537 | Spencer | Dec. 25, 1973 |
| U.S. | 3,804,077 | Williams | Apr. 16, 1974 |
| U.K. | 1,383,536 | Turner | Feb. 12, 1975 |
| U.S. | 3,874,504 | Verakas | Apr. 01, 1975 |
| U.S. | 3,885,403 | Spencer | May 27, 1975 |
| U.S. | 3,893,834 | Armstrong | July 08, 1975 |
| U.S. | 4,055,188 | Pelton | Oct. 25, 1977 |
| U.S. | 4,092,982 | Salem | June 06, 1978 |
| U.S. | 4,114,620 | Moore et al. | Sep. 19, 1978 |
| U.S. | 4,381,025 | Schooley | Apr. 26, 1983 |
| U.S. | 4,462,224 | Dunshee et al. | July 31, 1984 |
| U.S. | 4,596,250 | Beisang, III et al. | June 24, 1986 |

More recently, some compresses have been made microwavable so that they may be available more quickly than conventional compresses which need to be boiled before they are ready for use as hot therapy packs. Such microwavable compresses are shown in the following U.S. Patents:

| U.S. Pat. No. | Inventor(s) | Issue Date |
| --- | --- | --- |
| 4,488,552 | McCann et al. | Dec. 18, 1984 |
| 4,671,267 | Stout | June 09, 1987 |
| 4,756,311 | Francis, Jr. | July 12, 1988 |

However, such prior art compresses, either hot or cold or dual in nature, are usually made with thin plastic, such as polyethylene, which is clammy to touch and has an uncomfortable feeling for the user. Also, because their outer walls are usually very thin, such prior art compresses often diffuse their internal heat too quickly after they are first heated. Likewise, because their outer walls are so thin, such prior art compresses often warm up too quickly after they are first frozen. Accordingly, there are distinct disadvantages in using current state-of-the art hot compresses.

For example, Stout discloses a glove or mitten composite which is a reusable and microwavable hot or cold therapy mitt, but it does not have any apparent insulative layer therein. Thus, Stout's glove exemplifies the prior art disadvantages of diffusing heat too quickly when heated and warming up too quickly when frozen. Furthermore, Stout does not disclose any means for retaining his glove on the hand of the user.

SUMMARY OF THE INVENTION

It is a primary object of the present invention to provide a reusable and microwavable hot mitt which has on one side a dead air space and an intermediate insulative layer that allows a user to wear the mitt longer when a gel-filled pocket is hot and the mitt is ready to be worn on the hand. A sore muscle area of the hand may be the result of either a sports-related or a work-related injury.

It is a secondary object of the present invention to provide a reusable cold mitt which has on one side a dead air space and an intermediate insulative layer that allows a user to wear the mitt longer when a gel-filled pocket is solidly frozen and ready to be worn on the hand. Pain in the hand of an elderly user may be the result of arthritis.

It is a tertiary object of the present invention to provide a method of manufacturing such a mitt with an intermediate insulative layer and a dead air space on the side of the hand opposite to the gel-filled pocket so that either heat or cold can be retained longer between applications to the user's hand when wearing the hot or frozen mitt.

These and other objects and advantages of the present invention will become readily apparent from a study of the following brief description of the drawings and the subsequent detailed description of the preferred embodiment.

DETAILED DESCRIPTION OF THE PREFERRED EMBODIMENT

Figure 1:
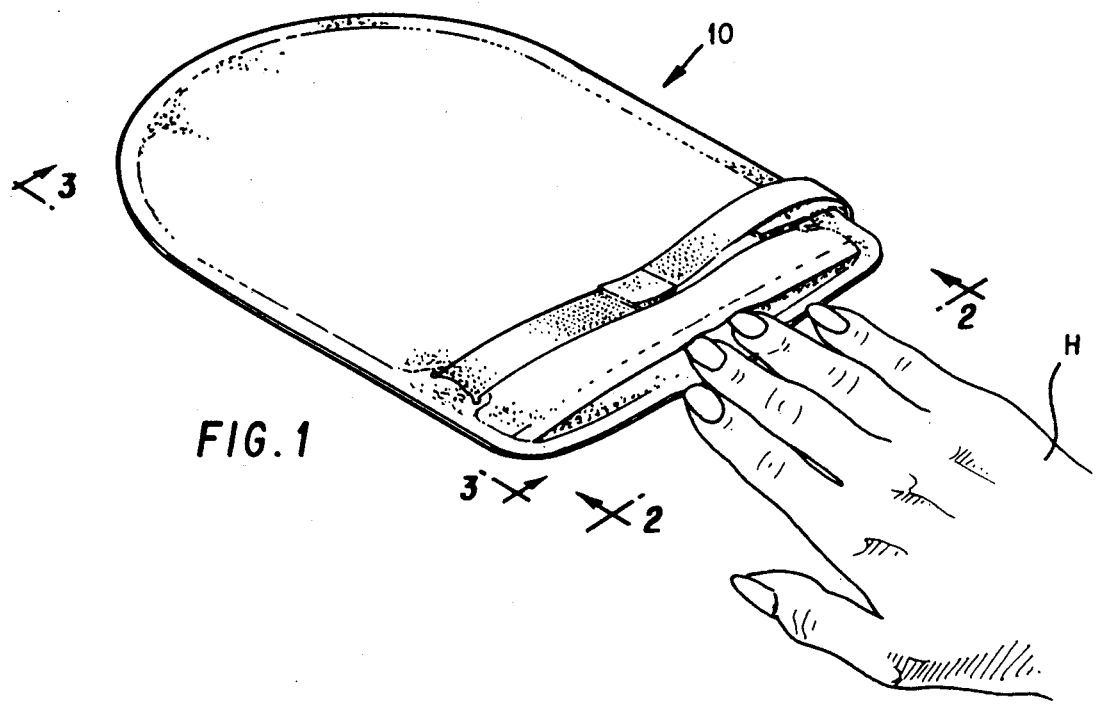
FIG. 1 is a perspective view of the mitt of the present invention being entered by the hand of a person.

In FIG. 1 of the drawings, there is shown a perspective view of a mitt 10 of the present invention into which a user is placing his or her hand H.

Figure 2:
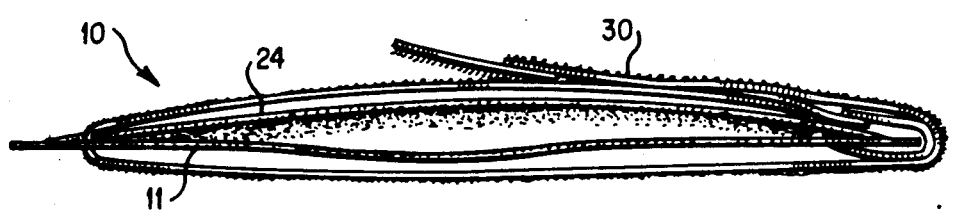
FIG. 2 is an end elevational view taken along line 2—2 in FIG. 1.

In FIG. 2, an end elevational view taken along line 2—2 in FIG. 1 shows a short side of the mitt 10. A bottom layer 11 of soft fabric is eight to ten mils thick and a top layer 24 of soft fabric is also eight to ten mils thick. A strap 30 serves as a fastener made of medium weight hook-and-loop type material, such as VELCRO.

Figure 3:
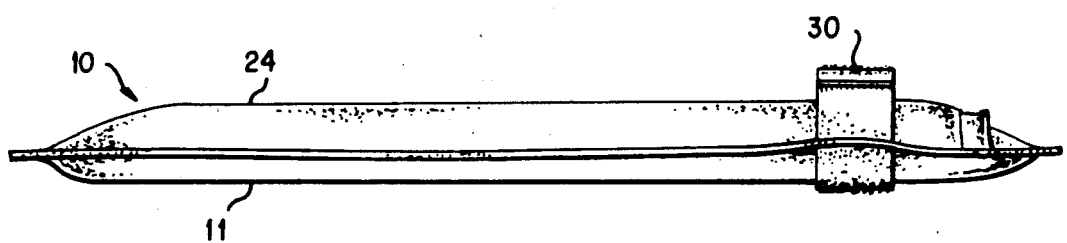
FIG. 3 is a left side elevational view taken along line 3—3 in FIG. 1.

In FIG. 3, a left side elevational view taken along line 3—3 of FIG. 1 shows a long side of the mitt 10. The bottom layer 11 and the top layer 24 of soft fabric are both visible. A right side elevational view showing only the bottom layer 11 and the top layer 24 of soft fabric would be a mirror image of this left side elevational view of the mitt 10, except for the appearance of the strap 30.

Figure 4:
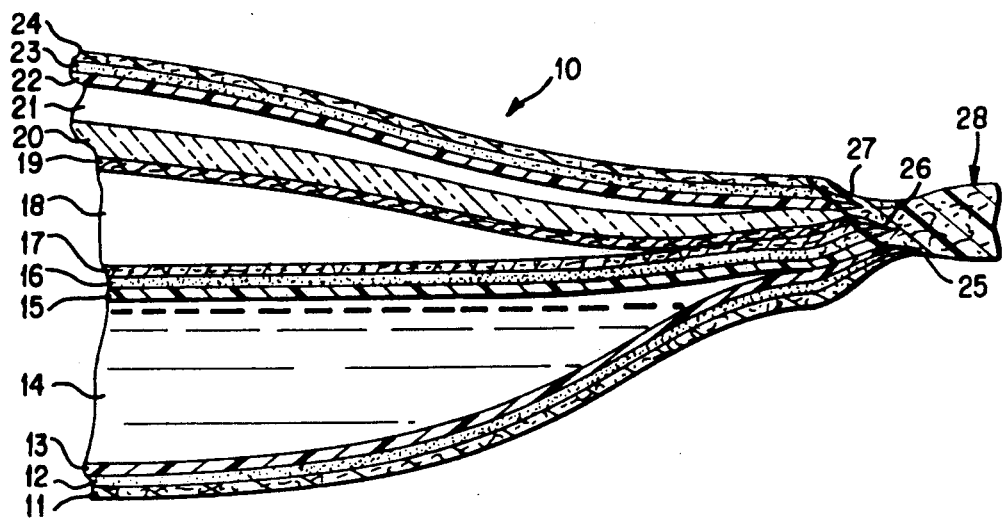
FIG. 4 is a partially broken away cross-sectional view of the mitt.

In FIG. 4, the long side of the mitt 10 shown in a left side elevational view is partially broken away and enlarged to illustrate the various layers of the invention in cross-section. The view of the layers in FIG. 4 will be discussed from bottom to top with the middle layers intended to be applied next to the affected part of the user's hand.

In FIG. 4, the first bottom layer 11 is made of soft fabric, such as polyester, nonwoven and interlocked. Next, there is a first bottom layer 12 of plastisol adhesive that is spread very thinly on a top surface of the layer 11 of the soft fabric. Then, a first bottom layer 13 of vinyl plastic is laid on top of the layer 12 of the plastisol adhesive so that the layer 13 of vinyl plastic adheres to the layer 11 of the soft fabric.

A gel 14 is later placed into a first pocket provided above the layer 13 inside the mitt 10. The first pocket is formed by a top surface of the first layer 13 of vinyl plastic and by a bottom surface of a second layer 15 of vinyl plastic.

Both freezable and heatable gels are known in the prior art. The heatable gel 14 used in the preferred embodiment of the present invention includes about 73 to 77 percent distilled water by weight, about 22 to 24 percent boiling point elevator by weight, and about one to five percent thickening agent by weight.

The preferred boiling point elevator is propylene glycol. The preferred thickening agent is an acrylic acid polymer powder, such as Carbopol 940, manufactured by the B. F. Goodrich Co. Other ingredients to suppress bacterial growth within the gel 14 and to enhance either processibility or shelf life may be added in amounts varying from one to four percent by weight, depending upon the combination of distilled water, boiling point elevator, and thickening agent.

The second middle layer 15 of vinyl plastic is provided with its bottom surface immediately above the first pocket containing the gel 14. Thus, the layer 15 is adjacent to the gel 14 in the mitt 10. A second middle layer 16 of plastisol adhesive is spread very thinly on a top surface of the layer 15 of vinyl plastic. Next, a second middle layer 17 of soft fabric is placed on top of the layer 16 of plastisol adhesive so that the layer 17 of soft fabric adheres to the layer 15 of vinyl plastic.

Next, an open air space 18 is provided in a second pocket as an opening for a user's hand above the layer 17 of soft fabric. The second pocket is formed by a top surface of the layer 17 of soft fabric and by a bottom surface of a sole layer 19 of open-celled soft fabric.

The sole layer 19 of open-celled soft fabric is provided with its bottom surface immediately above and adjacent to the open air space 18. A sole layer 20 of thick insulative wadding, such as needle-punched polyester, is placed on top of the sole layer 19 of open-celled soft fabric, but is not adhered thereto. The sole layer 20 of wadding is made at least thrice the thickness of the adjacent layer 19 of open-celled soft fabric in order to enhance the insulative ability of the wadding.

A dead air space 21 is then provided in a third pocket as an additional insulation above the layer 20 of wadding. The third pocket is formed by a top surface of the layer 20 of wadding and by a bottom surface of a third layer 22 of vinyl plastic.

The third top layer 22 of vinyl plastic is provided with its bottom surface immediately above and adjacent to the dead air space 21. A third top layer 23 of plastisol adhesive is spread very thinly onto a top surface of the layer 22 of vinyl plastic. Next, the third top layer 24 of soft fabric is placed on the layer 23 of plastisol adhesive so that the layer 24 of soft fabric adheres to the layer 22 of vinyl plastic. As indicated previously in the discussion of FIG. 2, the top layer 24 is eight to ten mils thick.

In the process of manufacturing the mitt 10, as can be readily seen from the right-hand side of FIG. 4, the first layer 11 of soft fabric is either bonded or laminated together with the first layer 13 of vinyl plastic by the first layer 14 of plastisol adhesive to form a bottom laminate 25.

Likewise, the second layer 15 of vinyl plastic is either bonded or laminated together with the second layer 17 of soft fabric by the second layer 16 of plastisol adhesive to form a middle laminate 26.

Similarly, the third layer 22 of vinyl plastic is either bonded or laminated together with the third layer 24 of soft fabric by the third layer 23 of plastisol adhesive to form a top laminate 27.

In the next step of the process for manufacturing the mitt 10, the bottom laminate 25, the middle laminate 26, the layer 19 of open-celled fabric, the layer 20 of thick insulative wadding, and the top laminate 27 are cut to size and heat-sealed together to form a coplanar outer edge 28, best seen on the left-hand side of FIG. 4, for the mitt 10.

The heat sealing of the three laminates 25, 26 and 27 together with the open-celled fabric layer 19 and the insulative wadding layer 20 to form the outer edge 28 is accomplished by radio-frequency (hereinafter RF) heating which essentially heats the internal molecular structure of the various plastic layers at 27.12 megahertz to cause an outer portion of each plastic layer to melt into the interstices of the fabric and wadding layers without scorching the outer surfaces of such fabric and wadding layers.

In the known prior art methods, various heat-sealing processes are known to scorch occasionally any fabric layers. The avoidance of scorching is an important advantage of the manufacturing process of the present invention over known prior art methods.

In other words, the outer edge 28 of the mitt 10 is formed by the RF heat-sealing of all coextensive plastic layers 13, 15 and 22 so that they melt into the bottom fabric layer 11, the middle fabric layer 17, and the top fabric layer 24, respectively.

This heat-sealing step is carried out around substantially the entire periphery of the outer edge 28 except for three openings which are left at one end of the mitt 10. These three openings form entrances into the first, second and third pockets, respectively, and are seen on the right-hand side of FIG. 4. Through the bottom opening, the gel 14 is squirted into the first pocket in the mitt 10. Through the middle opening, air is left to flow freely so that the user may be able to insert his or her hand easily into the second pocket. At the third opening, air is sealed in the third pocket to provide the dead space 21 inside the mitt 10. The squirting of the gel 14 into the first pocket and the seal of the air into the space 21 are steps that may be carried out either separately or simultaneously during the manufacturing process.

The final step of the method of the present invention involves RF heat-sealing of the first opening and the third opening so that the gel 14 and the dead air in the space 21 are securely sealed inside the mitt 10.

As a result of the last two manufacturing steps of creating the dead air space 21 and closing the third opening with RF heat, the mitt 10 is provided with a distinct advantage over the prior art when considered in conjunction with the earlier manufacturing step of superimposing the layer 20 of insulative wadding onto the layer 19 of open-celled fabric inside the mitt 10. This advantage is that either the heat or the cold emanating from the gel 14 is retained better in the open air space 18 provided for the user's hand.

Figure 5:
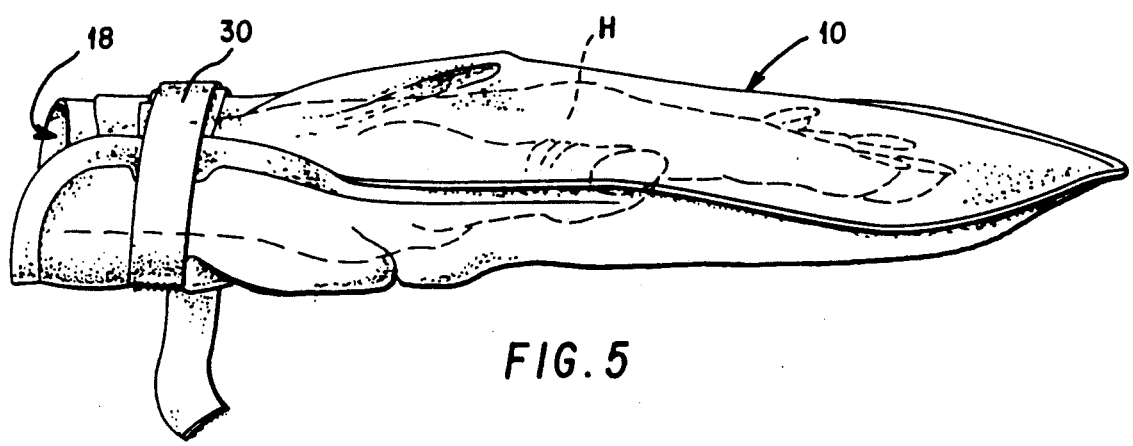
FIG. 5 is a perspective view of one use of the mitt to treat a hand that has either a sports-related injury or arthritis.

This advantage is best realized when viewing FIG. 5 in which the mitt 10 is secured on a user's hand H by the strap 30 so that either heat or cold is both radiated and reflected into an affected part of the user's hand H, without the need for any towels, paper cloths, and the like, which are likely to allow slippage of the mitt 10 onto the ground or floor, particularly when the user unconsciously drops the hand H to his or her side when walking.

Before using the present invention as shown in FIG. 5, a person will be able to distinguish the third pocket of dead air space 21 from the first pocket containing the gel 14, seen only in FIG. 4, because the insulated side of the third pocket of dead air space 21 will be less hot or cold to the touch of the user's hand H than the heated or frozen gel 14.

Furthermore, the user of the mitt 10 may place his or her hand H palm down, as seen in FIG. 5, or place the hand H into the second pocket of open air space 18 with the palm up, in order to permit either heat or cold to radiate more directly into the affected part of the hand H.

There are several other features that make the present invention more advantageous than known prior art devices.

First, the mitt 10 made by the above-described manufacturing method may incorporate layered plastic and fabric materials that are engineered to be expandable in order to allow for the escape of steam through the bottom laminate 25 containing the layers 11, 12 and 13 during the microwave heating of the mitt 10. In other words, the layers 11–13 are permeable to water vapor because the microscopic interstices function as pinholes to allow the release of steam from the heated gel 14, thus acting as a safety feature in the event that the user inadvertently overheats the mitt 10 either in a microwave oven or during heating in a conventional oven.

For example, the prior art compress which is the subject of U.S. Pat. No. 4,756,311 to Francis, Jr., is specifically claimed as a gel pack that does "not pass steam produced during heating . . . by microwave energy". Experiments have shown and it is tacitly admitted by the inventor, Mr. Francis, that this particular prior art compress is unfortunately likely to explode if heated in a microwave oven for more than four minutes.

A second advantageous feature of the present invention is that the layer 20 of insulative wadding and the dead air space 21 together function to prevent heat loss from the microwaved hot gel 14. Furthermore, they jointly serve to reflect the heat radiating from the hot gel 14 into the affected portion of the user's hand H shown in FIG. 5.

Similarly, the layer 20 of insulative wadding and the dead air space 21 together function to prevent cold loss from the frozen gel 14. Likewise, they jointly serve to retain the cold emanating from the frozen gel 14 so that the affected portion of the user's hand H continues to be cooled and relieved of pain for a period of time longer than the time afforded by known prior art compresses.

A third advantageous feature of the present invention is that, because the layer 20 of insulative wadding is inside the mitt 10 and is adjacent to the dead air space 21, the heat emanating from the microwaved hot gel 14 in a direction lateral to the affected portion of the user's hand H is reduced much more substantially than known prior art compresses having either an outer insulative layer or a single inner insulative layer. Such known prior art compresses with significant lateral emanation of heat are shown in the following references: U.S. Pat. No. 3,874,504 of Verakas; U.S. Pat. No. 3,893,834 of Armstrong; U.S. Pat. No. 4,596,250 of Beisang, III et al.; and U.K. Patent No. 1,383,536 of Turner.

A fourth advantageous feature of the present invention is that, because the outermost top layer 24 is made of soft fabric, this layer 24 can be easily printed upon in a decorative manner. Also, because the innermost layers 17 and 19 are likewise made of soft fabric, albeit two different types, they feel very comfortable to the user's hand H, seen in FIG. 5, while inside the mitt 10. Known prior art compresses, whether hot or cold, are usually made with outer layers of thin polyethylene plastic that is difficult to print upon. Furthermore, inner layers of such plastic are clammy to touch, thus giving an uncomfortable feeling to the user's hand.

A fifth advantageous feature of the present invention is that, because the layer 17 may be made of nonwoven or interlocked polyester fabric and the layer 19 may be made of open-celled fabrics which are capable of stretching both widthwise and lengthwise, the heated soft fabrics of layers 17 and 19 will not burn the user's hand, even if applied immediately after removal of the mitt 10 from the microwave oven. Because the layers 17 and 19 of soft fabrics are expandable, the soft fabrics allow the mitt 10 "to breathe." Thus, the innermost layers 17 and 19, which are the only layers to come into direct contact with the user's skin, are cool relative to the other layers.

A sixth advantageous feature of the present invention is that, because the outermot layer 24 is made of breathable fabric eight to ten mils thick, which is twice the normal thickness of most prior art compresses, the sole layer 20 of insulative wadding can be substantially reduced in thickness, thus reducing the bulk of the entire mitt 10 and lowering the packaging costs thereof. In most prior art compresses that have any kind of insulative layer, the outermost layer is usually nonbreathable plastic, thus requiring any insulative layer to be very thick and rendering the compresses very expensive to package, due to their bulk and the amount of air entrapped therein. Such thick insulative layers are shown in U.S. Pat. No. 4,596,250 to Beisang, III et al. and in U.K. Patent No. 1,383,536 to Turner.

The foregoing preferred embodiment is considered illustrative only. Numerous other modifications will readily occur to those persons skilled in this particular technology after reading this specification. Consequently, the disclosed invention is not limited to the exact structure and manufacturing method shown and described above, but rather is defined by the claims appended hereto.

What we claim as our invention is as follows:

1. A therapy mitt for a user's hand comprising:
a first layer of fabric having a top surface;
a first layer of adhesive spread on the top surface of the first layer of fabric;
a first layer of plastic adhered to the top surface of the first layer of fabric by the first layer of adhesive;
a first pocket means for containing a gel above the first layer of plastic;
a second layer of plastic being positioned above the first pocket means for containing the gel, said second layer of plastic having a top surface;
a second layer of adhesive spread on the top surface of the second layer of plastic;
a second layer of fabric adhered to the top surface of the second layer of plastic by the second layer of adhesive;
a second pocket means for providing an open air space for receiving the user's hand above the second layer of fabric;
a layer of open-celled material being positioned above the second pocket means for receiving the user's hand, said layer of open-celled material having a top surface;
a layer of insulative wadding provided on the top surface of the layer of open-celled material;
a third pocket means for providing a dead air space as additional insulation above the layer of insulative wadding;
a third layer of plastic positioned above the third pocket means for enclosing the dead air space. said third layer of plastic having a top surface;
a third layer of adhesive spread on the top surface of the third layer of plastic; and
a third layer of fabric adhered to the top surface of the third layer of plastic by the third layer of adhesive.

2. The therapy mitt, according to claim 1, wherein:
said first layer of fabric, said first layer of adhesive, and said first layer of plastic together form a bottom laminate below the gel contained in the first pocket means.

3. The therapy mitt, according to claim 1, wherein:
said second layer of plastic, said second layer of adhesive, and said second layer of fabric together form a middle laminate between the gel and the second pocket means for providing the open air space for receiving the user's hand.

4. The therapy mitt, according to claim 1, wherein:
said third layer of plastic, said third layer of adhesive, and said third layer of fabric together form a top laminate above the third pocket means for providing the dead air space as additional insulation.

5. The therapy mitt, according to claim 1, further comprising:
strap means for fastening the therapy mitt securely on the user's hand.

6. A therapy mitt for a user's hand comprising:
a bottom laminate;
a first pocket means for containing a gel above the bottom laminate;
a middle laminate being positioned above the first pocket means;
a second pocket means for providing an open air space for receiving the user's hand above the middle laminate;
a layer of open-celled material being positioned above the second pocket means, said layer of open-celled material having a top surface;
a layer of insulative wadding provided on the top surface of the layer of open-celled material;
a third pocket means for providing a dead air space as additional insulation above the layer of insulative wadding; and
a top laminate being positioned above the third pocket means.

7. The therapy mitt, according to claim 6, wherein:
said bottom, middle and top laminates each have outer peripheral edges that are RF heat-sealed together with outer peripheral edges of the layer of open-celled material and of the layer of insulative wadding.

8. The therapy mitt, according to claim 6, further comprising:
strap means for fastening the therapy mitt securely on the user's hand.

9. A method of manufacturing a therapy mitt for a user's hand, comprising the steps of:
providing a first layer of fabric having a top surface;
spreading a first layer of adhesive on the top surface of the first layer of fabric;
adhering a first layer of plastic to the top surface of the first layer of fabric by the first layer of adhesive;
containing a gel in a first pocket means arranged above the first layer of plastic;
positioning a second layer of plastic above the first pocket means for containing the gel, said second layer of plastic having a top surface;
spreading a second layer of adhesive onto the top surface of the second layer of plastic;
adhering a second layer of fabric to the top surface of the second layer of plastic by the second layer of adhesive;
providing a second pocket means with open air space for receiving the user's hand above the second layer of fabric;
positioning a layer of open-celled material above the second pocket means, said layer of open-celled material having a top surface;
placing a layer of insulative wadding on the top surface of the layer of open-celled material;
providing a third pocket means with a dead air space for additional insulating above the layer of insulative wadding;
positioning a third layer of plastic above the third pocket means provided with dead air space, said third layer of plastic having a top surface;
spreading a third layer of adhesive onto the top surface of the third layer of plastic; and
adhering a third layer of fabric to the top surface of the third layer of plastic by the third layer of adhesive.

10. The method, according to claim 9, comprising the further step of:

bonding together preliminarily the first layer of fabric, the first layer of adhesive, and the first layer of plastic to form a bottom laminate below the first pocket means for containing the gel.

11. The method, according to claim 9, comprising the further step of:

bonding together preliminarily the second layer of plastic, the second layer of adhesive, and the second layer of fabric to form a middle laminate between the first pocket means for containing the gel and the second pocket means provided with open air space for receiving the user's hand.

12. The method, according to claim 9, comprising the further step of:

bonding together preliminarily the third layer of plastic, the third layer of adhesive, and the third layer of fabric to form a top laminate above the third pocket means with the dead air space for additional insulating.

13. The method, according to claim 9, comprising the further step of:

attaching a strap to the therapy mitt so that the therapy mitt may be fastened securely on the user's hand.

14. A method of manufacturing a therapy mitt for a user's hand, comprising the steps of:

providing a bottom laminate;

containing a gel in a first pocket means above the bottom laminate;

positioning a middle laminate above the first pocket means;

providing a second pocket means with open air space for receiving the user's hand above the middle laminate;

positioning a layer of open-celled material above the second pocket means, said layer of open-celled material having a top surface;

placing a layer of insulative wadding on the top surface of the layer of open-celled material;

providing a third pocket means with dead air space for additional insulating above the layer of insulative wadding; and positioning a top laminate above the third pocket means.

15. The method, according to claim 14, comprising the further step of:

RF heat-sealing together the bottom, middle and top laminates along outer peripheral edges thereof with outer peripheral edges of the layer of open-celled material and of the layer of insulative wadding.

16. The method, according to claim 14, comprising the further step of:

attaching a strap to the therapy mitt so that the therapy mitt may be fastened securely on the user's hand.

* * * * *

UNITED STATES PATENT AND TRADEMARK OFFICE
CERTIFICATE OF CORRECTION

PATENT NO. : 5,050,596
DATED : September 24, 1991
INVENTOR(S) : Steven P. Walasek et al.

It is certified that error appears in the above-identified patent and that said Letters Patent is hereby corrected as shown below:

Title Page, left column, Section [63], line 2, change "1989." to --1989, now U.S. Pat. No. 5,035,241.--;

Section [56], line 4, change "Ellondrath" to --Eisendrath--;

Section [56], line 10, change "3,596,666" to --3,569,666--; and

Section [56], line 11, change "Aron" to --Arron--.

Title Page, right column, Section [57], ABSTRACT, line 10, change "insulating" to --insulation--.

Column 1, line 11, change "pending and" to --now U.S. Patent No. 5,035,241,--.

Column 4, line 13, delete "an".

Column 5, line 11, change "seal" to --sealing--;
line 16, after "14", insert --in the first pocket--; and

UNITED STATES PATENT AND TRADEMARK OFFICE
CERTIFICATE OF CORRECTION

PATENT NO. : 5,050,596
DATED : September 24, 1991
INVENTOR(S) : Steven P. Walasek et al.

It is certified that error appears in the above-identified patent and that said Letters Patent is hereby corrected as shown below:

Column 5, line 42, after "than", insert --the uninsulated top side of the first pocket containing--.

Column 6, line 58, change "outermot" to --outermost--.

Column 8, line 57, claim 9, change "insulating" to --insulation--.

Column 9, line 20, claim 12, change "insulating" to --insulation--.

Column 10, line 14, claim 14, change "insulating" to --insulation--.

Signed and Sealed this

Twenty-fifth Day of August, 1992

*Attest:*

DOUGLAS B. COMER

*Attesting Officer*  *Acting Commissioner of Patents and Trademarks*